US00PP18121P2

(12) United States Plant Patent
Olesen

(10) Patent No.: US PP18,121 P2
(45) Date of Patent: Oct. 9, 2007

(54) ROSE PLANT NAMED 'POULPAL020'

(50) Latin Name: *Rosa hybrida*
Varietal Denomination: Poulpal020

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/389,479

(22) Filed: Mar. 23, 2006

(51) Int. Cl.
*A01H 5/00* (2006.01)

(52) U.S. Cl. ..... Plt./131; Plt./140

(58) Field of Classification Search ..... Plt./131, Plt./140

See application file for complete search history.

*Primary Examiner*—Anne Marie Grunberg
*Assistant Examiner*—S. B. McCormick-Ewoldt

(57) ABSTRACT

A new garden rose plant of the compact floribunda class which has abundant, red flowers and attractive foliage. This new and distinct variety has shown to be uniform and stable in the resulting generations from asexual propagation.

1 Drawing Sheet

Botanical designation: *Rosa hybrida.*
Variety denomination: 'Poulpal020'.

SUMMARY OF THE INVENTION

The present invention constitutes a new and distinct variety of garden rose plant which originated from a controlled crossing between the female seed parent, 'Poulgrad', described and illustrated in U.S. Plant Pat. No. 11,610, and the male pollen parent, an unnamed seedling.

The two parents were crossed during the summer of 1997 and the resulting seeds were planted in a controlled environment in Fredensborg, Denmark. The new variety, named 'Poulpal020', originated as a single seedling from the stated cross.

The new variety may be distinguished from its female seed parent by the following combination of characteristics:

1. The seed parent has 25 to 30 flower petals. 'Poulpal020' has 80 petals total, 5 to 10 of which are petaloids.
2. Flowers of the seed parent have a general tonality of Red Group 53A to Red Group 46A. 'Poulpal020' has a general tonality of Red Group 46A.

The new variety may be distinguished from its male pollen parent by the following combination of characteristics:

1. The pollen parent has fewer flower petals than 'Poulpal020'.
2. The pollen parent is less compact in growth height than 'Poulpal020'.

The objective of the hybridization of this rose variety was to create a new and distinct variety for garden use with unique qualities, such as:

1. Uniform and abundant red flowers which do not fade;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal020' from all other varieties of which we are aware.

As part of the rose development program, Mogens N. Olesen germinated the seeds from the aforementioned hybridization during winter of 1997 and conducted evaluations on the resulting seedlings in a controlled environment in Fredensborg, Denmark. 'Poulpal020' was selected in the spring of 1998 by the inventor as a single plant from the progeny of the aforementioned hybridization.

Asexual reproduction of 'Poulpal020' by traditional budding and rooted cuttings was first done by Mogens N. Olesen in the nursery in Fredensborg, Denmark in July, 1998. This initial and other subsequent asexual propagations conducted in controlled environments have demonstrated that the characteristics of 'Poulpal020' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulpal020'. Specifically illustrated in the drawing are.

DETAILED DESCRIPTION OF THE VARIETY

Figures 1A, 1B, 1C, 1D, 1E, 1F:
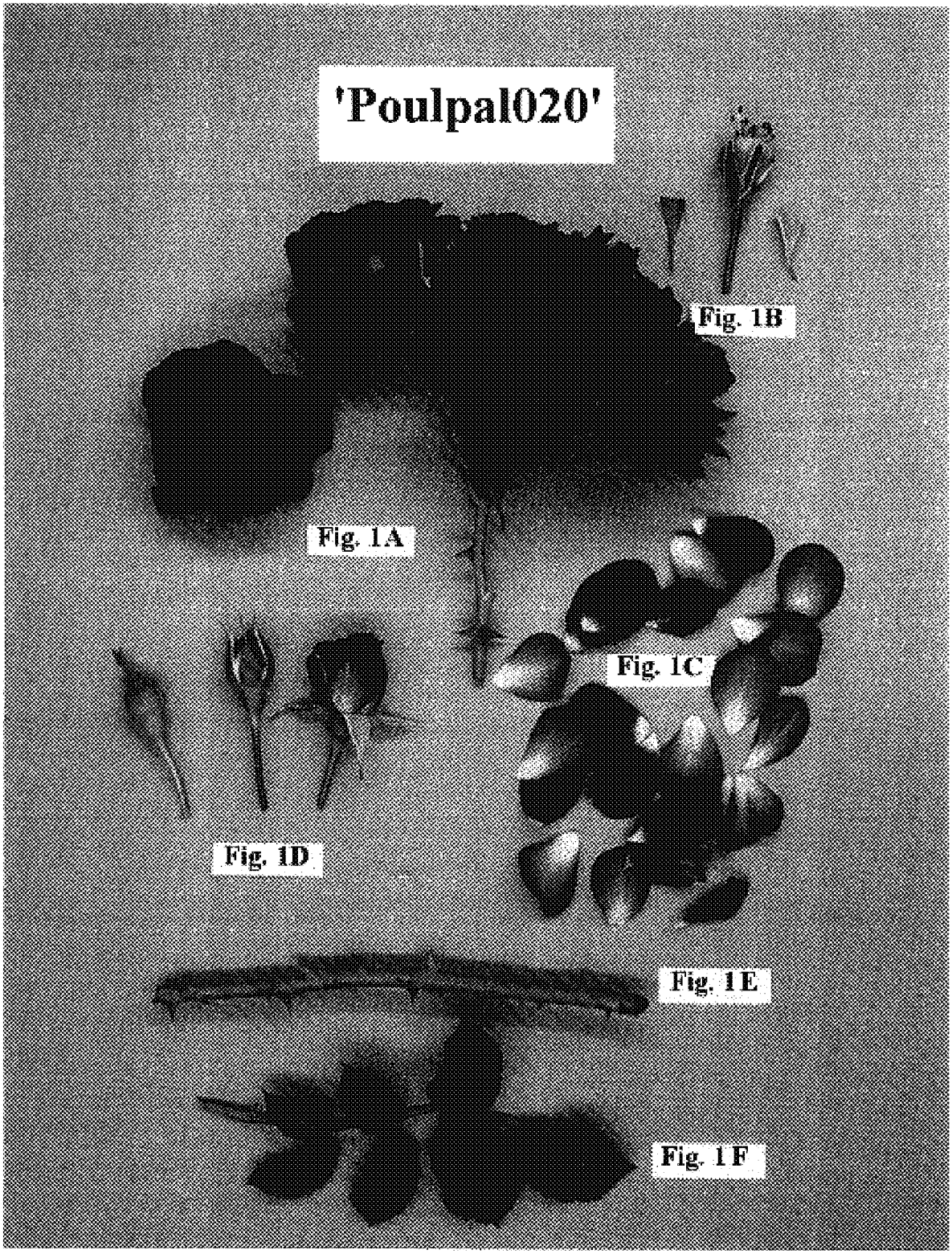
FIG. 1A; Open flower, stem showing cluster of open flowers.
FIG. 1B; Sepals, receptacle, peduncle, and reproductive flower parts.
FIG. 1C; Flower petals, detached.
FIG. 1D; Flower buds at various stages of development.
FIG. 1E; Bare stem exhibiting prickles.
FIG. 1F; Mature leaf.

The following is a description of 'Poulpal020', as observed in its growth in in a field nursery in Jackson County, Oreg. Observed plants are 2 years of age, and were grown on *Rosa multiflora* understock. Color references are made using The Royal Horticultural Society (London, England) Colour Chart, 2003, except where common terms of color are used.

For a comparison, several physical characteristics of the rose variety 'Poulchris', U.S. Plant Pat. No. 11,151, are compared to 'Poulpal020' in Chart 1.

CHART 1

| | 'Poulpal020' | 'Poulchris' |
|---|---|---|
| Petal Count | 80, 5 to 10 of which are petaloids | 55 to 65 |
| Flower Diameter | 50 mm | 60 mm |
| Upper petal surface color | Red Group 45A to 46A with occasional streaking of Red Group 55D | Red Group 53A |

FLOWER AND FLOWER BUD

Blooming habit: Continuous.

Flower bud:

*Size.*—Upon opening, 20 mm in length from base of receptacle to end of bud. Bud diameter is 12 mm.

*Bud form.*—Urceolate.

*Bud color.*—As sepals unfold, petals are Red-Purple Group 58A.

*Sepals.*—Sepal inner surface: Color: Green Group 138A to 138B. Medium anthocyanic pigments of Greyed-Purple 183A. Surface: Medium pubescence observed. Sepal outer surface: Color: Yellow-Green Group 144A. Anthocyanic pigments Greyed-Red Group 181A color of observed. Texture: Smooth. Sepal Shape: Apex: Cirrhose. Base: Flat at union with receptacle. Sepal Margin: Margins have medium foliaceous appendages on three of the five sepals. Sepal size: 20 mm long by 6 mm wide. Receptacle: Texture: Smooth. Shape: Urn-shaped. Size: 12 to 13 mm (h)×7 mm (w). Color: Yellow-Green Group 144A. Light anthocyanic pigments the color of Greyed-Red Group 181A observed. Pedicel: Surface: Slightly rough with stipitate glands. Length: 35 to 40 mm on average. Diameter: 2 mm on average. Color: Yellow-Green Group 146B. Light anthocyanic pigments the color of Greyed-Purple Group 183A observed. Strength: Strong.

Flower bud development: Flower buds are borne in clusters of 7 flower buds per stem. Arrangement resembles a panicle.

Flower bloom:

*Fragrance.*—None.

*Duration.*—the blooms have a duration on the plant of approximately 10 days. Petals fall cleanly away from plant after flowers have fully matured.

*Size.*—Flower diameter is 50 mm when open. Flower depth is 20 to 25 mm.

*Flower shape.*—General shape is a rosette, very double flower with many slightly overlapping petals of different sizes.

*Shape of flower, side view.*—Upon opening the upper portion is flattened convex. The lower portion is concave. After opening, the upper portion is flattened convex. The lower portion is concave.

*Petalage.*—Under normal conditions, flowers have 80 petals total, 5 to 10 of which are petaloids.

*Petal color.*—Upon opening, outer petals Upper surface: Red Group 53A with intonations of Red-Purple Group 59A. Lower surface: Red-Purple Group 60C to 60D at margins. Intonations of White Group N155A blend with Red and Red-Purple at the middle zone, becoming completely White Group N155A at the basal zone. Upon opening, inner petals: Upper surface: Red Group 46A with intonations of Red-Purple Group 60A. Lower surface: Red-Purple Group 60C to 60D at margins. Intonations of White Group N155A blend with Red and Red-Purple at the middle zone, becoming completely White Group N155A at the basal zone. Basal petal spots, upon opening: Upper surface: White Group 155A. Yellow Group 3C at point of attachment. Lower surface: Yellow Group 3D. After opening, outer petals Upper surface: Red Group 45A with intonations of Red Group 46A with occasional streaking colored Red Group 55D. Lower surface: Red-Purple Group 60C to 60D at the petal margins. White is blended in at the middle zone progressing to become completely White Group N155A at the basal zone. After opening, inner petals: Upper surface: Red Group 45A with intonations of Red Group 46A occasional streaking colored Red Group 55D. Lower surface: Red-Purple Group 60C to 60 D at the petal margins. White is blended in at the middle zone progressing to become completely White Group N155A at the basal zone. Basal petal spots, after opening: Upper surface: Yellow Group 1D. Lower surface: Yellow Group 2D.

General tonality: On open flower Red Group 46A. No change in the flower tonality as flowers mature.

Petals:

*Petal reflex.*—Somewhat reflexed.

*Margins.*—Entire with occasional point at the center.

*Shape.*—Generally narrow elliptical in shape. Apex shape: Rounded. Base shape: Acute.

*Size.*—Outer petals: 27 mm (l)×19 mm (w). Inner petals: 15 m (l)×8 mm (w).

*Texture.*—Smooth.

*Thickness.*—Average.

*Arrangement.*—Not Formal.

Petaloids:

*Quantity.*—5 to 10.

*Shape.*—Irregular.

*Color.*—Red Group 46A.

*Size.*—11 mm (l)×7 mm (w).

Reproductive organs:

*Pollen.*—None observed.

*Anthers.*—Size: 2 mm in length. Color: Yellow-Orange Group 15A. Quantity: Normally 70.

*Filaments.*—Color: Yellow Group 13B. Length: 4 mm.

*Pistils.*—Length: 4 mm. Quantity: Normally 35.

*Stigmas.*—Level in location relative to the length of the filaments and the height of the anthers. Color: Yellow-White Group 158B.

*Styles.*—Color: Red-Purple Group 58A.

*Hips.*—None Observed.

PLANT

Plant growth: Compact, upright, and bushy. When grown as a budded field grown plant on *Rosa multiflora* understock, the average height of the plant is 40 to 60 cm and the average width is 45 cm.

Stems:

*Color.*—Juvenile growth: Yellow-Green Group 144B with no anthocyanic intonations. Mature growth: Green Group 138A.

*Length.*—On average, canes at 30 to 40 cm from the base of the plant to the flowering portion.

*Diameter.*—Normally 7 mm.

*Internodes.*—On mature canes, there is an average distance of 30 mm between nodes.

*Surface texture.*—Young wood: Smooth. Older wood: Smooth.

Prickles:

*Incidence.*—70 to 100 prickles per 10 cm of stem on mature wood.

*Size.*—Average lengthy of prickles on mature stems is 8 mm.

*Shape.*—Concave to flat.

*Color.*—Juvenile prickles: Greyed-Yellow Group 160A with intonations of Greyed-Red Group 179A. Mature prickles: Greyed-Orange Group 175A and Yellow-Green Group N144A.

Plant foliage: Normally 7 leaflets on leaves in middle of the stem.

*Compound leaf.*—100 to 125 mm (l)×55 to 90 (w).

*Quantity.*—3 leaves per 10 cm of stem on average.

*Color of mature foliage.*—Upper side: Yellow-Green Group 147A. Lower side: Yellow-Green Group 147B to 147C.

*Color of juvenile foliage.*—Upper side: Yellow-Green Group 144A. Lower side: Yellow-Green Group 144B. Anthocyanic intonations: Greyed-Red Group 180A. Location: Margins.

Plant leaves and leaflets:

*Stipules.*—Size: 25 to 30 mm in length. Shape: Linear, slightly broad based with outward extending apecies. Margins: Finely serrated with many stipitate glands. Color: Yellow-Green Group 144A.

*Petiole.*—Length: 32 to 36 mm. Diameter: 2 mm.

*Upper surface.*—Color: Yellow-Green Group 146A. Observations: Numerous stipitate glands.

*Lower surface.*—Color: Yellow-Green Group 145B. Observations: Few prickles observed.

*Rachis.*—Length: 45 to 55 min. Upper surface: Color: Yellow-Green Group 146A. Observations: Numerous stipitate glands.

*Lower surface.*—Color: Yellow-Green Group 145B. Observations: Numerous small prickles observed.

*Leaflet.*—Edge: Doubly serrated. Size: Average size of the terminal leaflet on normal leaves is 30 to 40 mm in length by 26 to 32 mm wide. Shape: Generally Rounded. Base: Rounded to somewhat cordate. Apex: Cuspidate. Texture: Rugose. Thickness: Thick. Arrangement: Odd pinnate. Venation: Reticulate. Glossiness: Somewhat glossy.

Disease resistance: Above average resistance to powdery and downy mildew, rust, black spot, and *Botrytis* under normal growing conditions in Jackson County, Oreg.

Cold hardiness: The variety is tolerant to USDA Cold Hardiness Zone 6.

Heat tolerance: The variety has been found to be suitable for climate conditions found in the American Horticulture Society heat zone 7.

It is claimed:

1. A new and distinct variety of rose plant of the compact floribunda rose class named 'Poulpal020', substantially as illustrated and described herein, due to its abundant red flowers, disease resistance, and extended period of bloom.

* * * * *

'Poulpal020'